US006796984B2

United States Patent
Soubeiran

(10) Patent No.: US 6,796,984 B2
(45) Date of Patent: Sep. 28, 2004

(54) DEVICE FOR RELATIVE DISPLACEMENT OF TWO BODIES

(76) Inventor: André Arnaud Soubeiran, 24 Villa de Lourcine 75014, Paris (FR)

(*) Notice: Subject to any disclaimer, the term of this patent is extended or adjusted under 35 U.S.C. 154(b) by 237 days.

(21) Appl. No.: 10/203,943
(22) PCT Filed: Feb. 21, 2001
(86) PCT No.: PCT/FR01/00496
 § 371 (c)(1),
 (2), (4) Date: Aug. 16, 2002
(87) PCT Pub. No.: WO01/64119
 PCT Pub. Date: Sep. 7, 2001

(65) Prior Publication Data
US 2003/0032958 A1 Feb. 13, 2003

(30) Foreign Application Priority Data
Feb. 29, 2000 (FR) .................................. 00 02556

(51) Int. Cl.⁷ .............................................. A61B 17/56
(52) U.S. Cl. ............................ 606/61; 606/63; 606/78
(58) Field of Search ................. 606/61, 63; 623/18.12, 623/23.47

(56) References Cited

U.S. PATENT DOCUMENTS 5,720,746 A * 2/1998 Soubeiran .................. 606/61

* cited by examiner

*Primary Examiner*—Kevin Shaver
*Assistant Examiner*—Candice C. Melson
(74) *Attorney, Agent, or Firm*—Sughrue Mion, PLLC

(57) ABSTRACT

The present invention relates to devices for moving a two bodies 1, 2 relative to each other. The device of the invention is essentially characterized by the fact that it comprises two parts 11, 12, a projecting portion 14 mounted to co-operate with one of the two parts, a cavity 13 formed in the other part and complementary in shape to the projecting portion 14, the two parts 11, 12 being mounted to move relative to each other in such a manner that the projecting portion 14 penetrates into the cavity 13, the projecting portion 14 forming a closed loop made of an electrically conductive material which completely surrounds a magnetic core 101 which is not completely surrounded by the mechanism 100 for interconnecting the projecting portion 14 and the first part 11. The invention is applicable in particular to a bone prosthesis, a medullary nail for lengthening bones, a rod for correcting and supporting the spinal column.

8 Claims, 1 Drawing Sheet

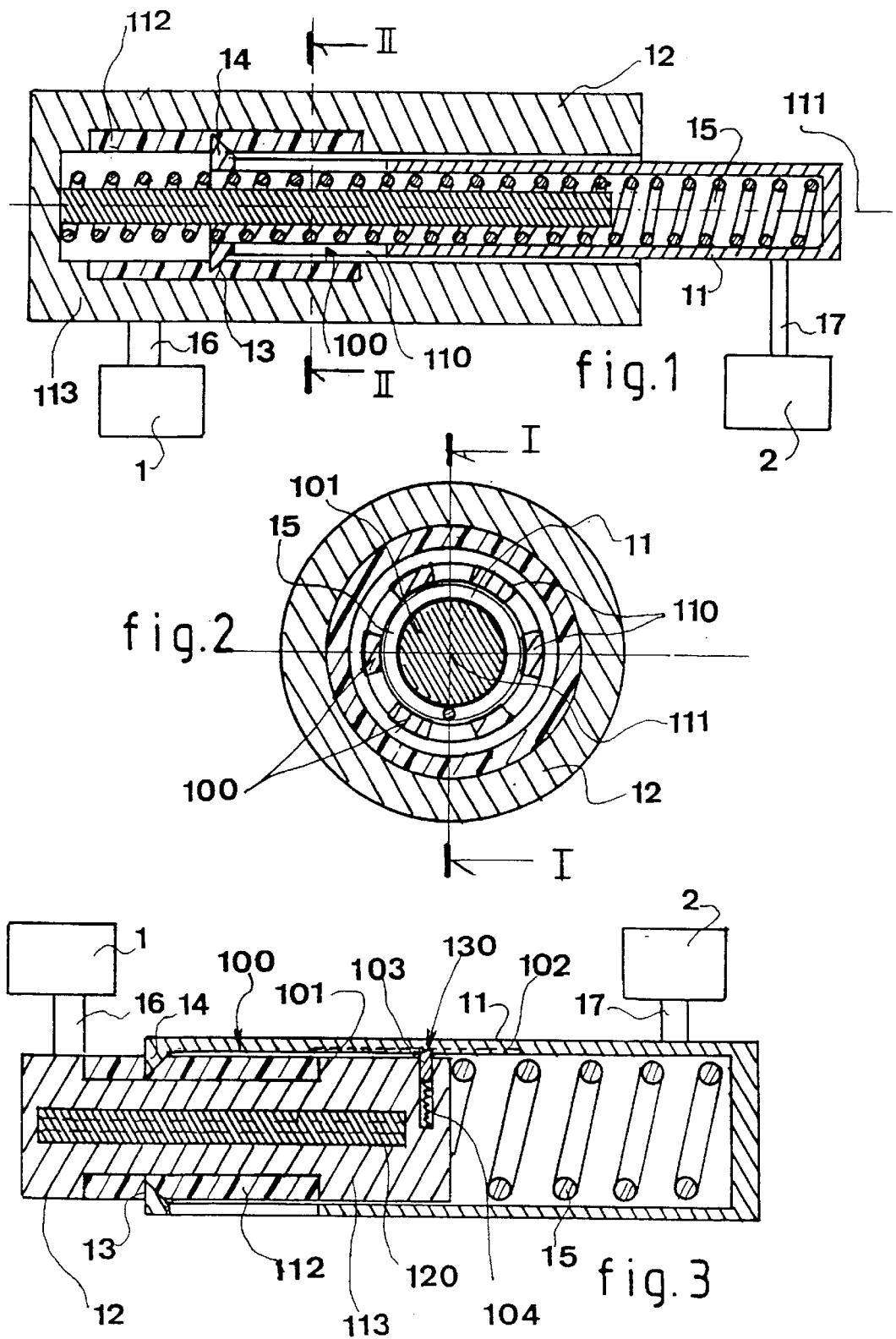

DEVICE FOR RELATIVE DISPLACEMENT OF TWO BODIES

The present invention relates to an improvement to devices for moving one body relative to another, in particular those which have advantageous applications in making systems for implanting in the human body or the like.

A device for moving one body relative to another is already known, in particular from document WO 96/15377 in the name of the Applicant, which device is advantageously applied to making systems that are implantable in the human body or the like.

The device described in that prior document gives good results. Nevertheless, the present invention seeks to improve that device, enabling its structure to be made more compact and its strength to be even greater, and making it easier to manufacture using commonplace means both in industrial production and for particular circumstances. Another object of the present invention is to improve the device of the above-specified prior document by enabling users to be informed by means of a simple signal of progress in the displacement of one body relative to the other while avoiding any need to make use of external means for verification purposes such as X-rays, and enabling the two bodies to be positioned relative to each other even more accurately during their displacements, and which is suitable for being controlled by an apparatus that is simple to make, and small in size, regardless of the ordinary application under consideration.

More precisely, the present invention provides a device for displacing a first body relative to a second body, the device comprising: first and second parts, means for applying a force between said first and second parts, a projecting portion, means for connecting said projecting portion to the first part, a cavity made in the second or other part, said cavity being complementary in shape to at least a fraction of said projecting portion, the second part in which said cavity is made being of a first material suitable for passing from a non-deformable first state to a deformable semisolid second state, and vice versa, the non-deformable solid state being a state in which said projecting portion cannot deform said first material under drive from said force, and the deformable semisolid state being a state in which said projecting portion is capable, under drive from said force, of penetrating into said first material so that said first material creeps around said projecting portion, while the first part carrying said projecting portion is made of a second material that is substantially non-deformable, said first and second parts being mounted to move relative to each other in such a manner that said first portion penetrates into said cavity, and means for controlling the transition of the portion of first material surrounding said cavity from said first state to the second, and vice versa, the device being characterized by the fact that said projecting portion forms a closed loop made of an electrically conductive material which completely surrounds a magnetic core, which core is not completely surrounded by the means for connecting said projecting portion to the first part.

Other characteristics and advantages of the invention appear from the following description given with reference to the accompanying drawing by way of non-limiting illustration, and in which:

FIGS. 1 and 2 are section views of a first embodiment of the device of the invention particularly adapted to making a bone prosthesis, FIG. 1 being a section on plane referenced I—I in FIG. 2 and FIG. 2 being a section on plane referenced II—II in FIG. 1, and the scale of FIG. 2 being larger than that of FIG. 1; and FIG. 3 is a longitudinal section of a second embodiment of the device of the invention which is particularly advantageous for use as a medullary nail for lengthening a bone and as a rod for correcting and supporting the vertebral column.

FIGS. 1 to 3 show two preferred embodiments of the improved device of the invention. In these two embodiments, reference is made to two bodies 1 and 2 as described in above-mentioned WO 96/15377. The body 1 is connected by means 16 of any kind to a part 12 having a cavity 13, while the body 2 is connected by means 17 of any kind to a part 11 which has a projecting portion 14 of continuous annular shape and penetrating at least in part into the cavity 13. These connection means 16 and 17 can be constituted, for example, in the same manner as those described in the above-referenced prior document.

According to an important characteristic of the invention, the improved device further comprises a bar 101 of soft magnetic material which is arranged to be constantly situated as a function of any possible displacement of the two bodies 1 and 2 substantially in the center of the closed loop constituted by the projecting portion 14.

In known manner, in particular as described in the above-identified prior document, the device also comprises means for applying a resilient force between the two parts 11 and 12, for example a spring 15 or a combination of springs. These means are shown in FIGS. 1 and 3 and are fully defined in the prior document.

According to another important characteristic of the invention, the device comprises means 100 for connecting the projecting portion 14 to the first part 11, which means do not form a loop around the bar 101 of soft magnetic material. These means 100 for connecting the projecting portion to the first part therefore do not completely surround the magnetic core.

These means 100 are advantageously constituted by at least one tab 110 extending substantially parallel to the axis 111 of the projecting portion 14 in the form of a closed loop, preferably by a plurality of tabs 110 that are substantially regularly distributed around said axis 111, as can be seen more particularly in FIG. 2. In a plane perpendicular to the axis 111 of projecting portion 14, these tabs 110, which are substantially parallel to one another and to the above-defined axis 111, form an open structure between said projecting portion 14 and the part 11, which open structure limits the amount of electrical current that is induced in the connection 100 between the projecting portion 14 and the part 11.

When the device has a plurality of tabs 110 as shown in FIGS. 1 and 2, then the gaps between the tabs 110 can be filled with an electrically insulating material that withstands heat. By way of example this material can be silicone, or a ceramic, such as zirconia ceramic, etc.

In the embodiment shown in FIG. 1, there are situated around the bar 101 of soft magnetic material in order from the closest to the bar to the furthest away: the spring 15, the part 11 carrying the outwardly-directed projecting portion 14, and the part 12 having the cavity 13.

In the embodiment shown in FIG. 3, there are situated around the bar 101 of soft magnetic material, from the closest to the bar to the furthest away: the part 12 having the cavity 13, the projecting portion 14 which in this case is inwardly-directed, and the part 11 carrying the projecting portion 14, it being emphasized that in this embodiment, the spring 15 does not surround the bar 101 but is compressed between the part 11 and the part 12.

The embodiments shown are preferably bodies of revolution and the various elements are advantageously coaxial, being distributed around the bar 101 of soft magnetic material.

In the embodiment shown in FIG. 3, the device has means 130 suitable for emitting a sound signal each time the part 11 moves through a step of given size relative to the part 12 (or vice versa).

In a preferred embodiment, these means 130 are constituted, as shown in FIG. 3, by a ratchet system with the pawl 103 of the system being mounted to cooperate with the part 2 and with the rack 102 with which the pawl co-operates being secured to the part 11. Each time the part 11 moves as specified in the above-defined prior document, the pawl rises up a tooth, and when it drops between two teeth of the rack it makes a click sound. Each click corresponds to a step of determined size which is exactly the distance between two teeth of the rack. By counting the number of clicks made by the pawl, the user can be fully aware of the total displacement of the two parts 11 and 12 relative to each other.

The clicks emitted by the pawl 103 as it moves along the rack 102 indicate that the two parts 11 and 12 are moving relative to each other and make it possible to avoid using other means for verifying that such displacement has taken place, such as those used in the prior art which are generally complex and expensive.

The improved device can further comprise means for guiding the part 12 in translation and in rotation relative to the part 11, while guaranteeing that the pawl 103 remains continuously in register with the rack 102 throughout such displacement. These means can be of any kind, for example constituted by a finger secured to one of the two parts and a groove made in the other part, the finger sliding along the groove. These means are not shown specifically since they are known in themselves and making them presents no difficulty for the person skilled in the art.

Nevertheless, the pawl 103 and the rack 102 can be circular, thus eliminating any need to provide rotary guidance between the two parts 11 and 12 when that is not desirable.

The force tending to press the pawl 103 against the rack 102 can be delivered by a spring 104 as shown in FIG. 3, for example, or by an elastically-deformable zone of the part carrying the pawl, or by a resilient portion of the pawl itself, or by any other means known to the person skilled in the art.

Clearly various other combinations of pawl and rack are possible although not shown. In particular, a plurality of pawls can co-operate with the same rack. The rack and the pawl can also be secured to portions of the device other than those selected for the embodiments shown in the figures, and still produce the same effect.

Also, the embodiment of the improved device as shown in FIG. 1 can benefit from the same pawl and rack combinations as those defined above and shown by way of example in FIG. 3.

The bodies 1 and 2 and their connection means 16 and 17 connecting them to the parts 11 and 12 can be of any type. If they completely surround the bar 101 of soft magnetic material, they are advantageously made of materials that are electrically insulating and nonmagnetic.

The part 11 carrying the projecting portion 14, said projecting portion 14, and the tabs 110 are preferably made as a single piece of a mechanically strong metal, and in the application of the device as a prosthesis implantable in a living body, and in particular in a human body, a metal which is tolerated well by the living body, such as titanium or stainless steel.

The part 12 or the portion 112 of the part 12 in which the cavity 13 is formed is made for example out of a polymer such as polyethylene (PE) or polyacetal (POM), the portion 112 being contained for example in a complementary part 113 of a stronger material such as poly ether ether ketone (PEEK) or the like.

The springs 15 are preferably made of a material having very great strength, such as Phynox (registered trademark).

The soft magnetic material constituting the bar 101 can be constituted, for example, by soft ferrite, preferably without nickel, or advantageously by a compound comprising such a ferrite in powder form and a polymer that is well tolerated by the living body such as poly ether ether ketone (PEEK).

The bar 101 made of soft magnetic material can be tubular and in its center it can receive a rod 120 shown diagrammatically in dashed lines in FIG. 3, e.g. a metal rod providing mechanical reinforcement and giving it good stiffness. Advantageously, the bar can be made by overmolding, extruding, or sintering powder directly around the metal rod. The bar as reinforced in this way is suitable not only for guiding magnetic field lines, but also, for example, for guiding the spring 15 or the spring system constituting the means for applying a resilient force between the two parts 11 and 12 in the embodiment of the improved device of the invention as shown in FIG. 1, or for providing mechanical reinforcement, particularly in bending, for the part 12 in which the cavity 13 is provided in the embodiment of the improved device as shown in FIG. 3. The part 12 in which the cavity 13 is formed may itself in the embodiment shown in FIG. 3 be overmolded or extruded directly around the bar, for example.

The length of the bar is not less than the length of the total desired displacement stroke of the two parts 11 and 12 relative to each other, and advantageously it is slightly longer.

The projecting portion 14 and the bar 101 of soft magnetic material are preferably bodies of revolution about a common axis, even when the other elements of the device are not bodies of revolution.

The above-described improved device is controlled by induction heating of the annular projection portion 14 in the presence of the bar 101 of soft magnetic material, the device being placed in a magnetic field that varies rapidly in time, as obtained by means of a coil whose axis coincides substantially with that of the bar 101 which serves to concentrate the magnetic field lines, and occupying a plane that intersects the bar 101 at a point that is not completely masked by the part 11 carrying the projecting portion 14. The coil must be large enough to surround the device completely together with any container (and in particular the portion of the living body in which it is implanted, such as a leg) and it comprises a few turns to a few tens of turns.

The coil then carries electrical current of frequency and magnitude that are appropriate to ensure that the projecting portion 14 is heated by induction, and in turn acts by conduction to heat the portion of the part 12 which surrounds the cavity 13, thereby softening it.

The means such as a spring or a spring system 15 for applying a resilient force between the two parts 11 and 12 can thus come into action and drive the desired displacement of the two parts.

The running dimensions of the projection are generally about 8 millimeters (mm) to 30 mm in diameter and about 1 square millimeter ($mm^2$) to 10 $mm^2$ in section. The projection, the tabs, and the part to which they are secured can be made out of a material known under the references Ti 6Al 4V or 316L, for example. The preferably nickel-free soft ferrite has, for the most part, relative permeability of a few hundreds.

For the usual applications of the device as a prosthesis, a medullary nail or a spine rod, a coil having an inside diameter of about 16 centimeters (cm) and comprising ten to 20 turns of wire subdivided into 100 strands each having a diameter of 0.2 mm and carrying an electrical current at a frequency lying in the range 80 kHz to 150 kHz with peak amplitude of 60 amps (A) to 110 A, is well adapted to heating the projection 14 and thus to controlling the device.

Such electrical current can be obtained by connecting the coil to a capacitor, either in parallel or in series, and by exciting the inductance-capacitance (LC) resonant circuit constituted in this way at a frequency close to its resonant frequency by means of a suitable adaptor. The capacitance of the capacitor is determined so that the resonant frequency lies in a range of excitation frequencies suitable for induction heating the projecting portion 14, and taking account of the available soft magnetic material.

The improved device of the invention can easily be made by the person skilled in the art using conventional means for shaping the various materials used, such as milling, turning, or injection molding, for example. The device is particularly adapted to making nails for lengthening bones, rods for correcting and supporting the spinal column, and bone prostheses for children.

What is claimed is:

1. A device for displacing a first body (1) relative to a second body (2), the device comprising: first and second parts (11, 12), means (15) for applying a force between said first and second parts, a projecting portion (14), means (100) for connecting said projecting portion (14) to the first part (11), a cavity (13) made in the second or other part (12), said cavity (13) being complementary in shape to at least a fraction of said projecting portion (14), the second part (12) in which said cavity (13) is made being of a first material suitable for passing from a non-deformable first state to a deformable semisolid second state, and vice versa, the non-deformable solid state being a state in which said projecting portion (14) cannot deform said first material under drive from said force, and the deformable semisolid state being a state in which said projecting portion (14) is capable, under drive from said force, of penetrating into said first material so that said first material creeps around said projecting portion (14), while the first part (11) carrying said projecting portion (14) is made of a second material that is substantially non-deformable, said first and second parts (11, 12) being mounted to move relative to each other in such a manner that said first portion (14) penetrates into said cavity (13), and means for controlling the transition of the portion of first material surrounding said cavity (13) from said first state to the second, and vice versa, the device being characterized by the fact that said projecting portion (14) forms a closed loop made of an electrically conductive material which completely surrounds a magnetic core (101), which core is not completely surrounded by the means (100) for connecting said projecting portion (14) to the first part (11).

2. A device according to claim 1, characterized by the fact that said magnetic core (101) is constituted by a bar of soft magnetic material.

3. A device according to claim 2, characterized by the fact that said bar (101) is in the form of a tube, and contains within the tube a reinforcing rod (120).

4. A device according to claim 1, characterized by the fact that the means (100) for connecting said projecting portion (14) to the first part (11) comprise a plurality of tabs (110) that are substantially regularly distributed around said bar (101) and substantially parallel to one another.

5. A device according to claim 1, characterized by the fact the projecting portion (14), the first part (11), and the means (100, 110) for connecting them together are all made of the same material.

6. A device according to claim 1, characterized by the fact that it comprises means (130) suitable for emitting a sound signal each time the two parts (11, 12) move relative to each other through a step of given size.

7. A device according to claim 6, characterized by the fact that the means (130) suitable for emitting a sound signal each time the two parts (11, 12) move relative to each other to a step of given size, are constituted by a ratchet system comprising at least one pawl (103) secured to one of the two parts (12) and a rack (102) secured to the other part (11).

8. A device according to claim 7, characterized by the fact that it includes means for guiding the second part (12) in translation relative to the first part (11).

* * * * *